(12) United States Patent
Umemoto et al.

(10) Patent No.: US 9,192,289 B2
(45) Date of Patent: Nov. 24, 2015

(54) ENDOSCOPE SYSTEM

(71) Applicant: OLYMPUS MEDICAL SYSTEMS CORP., Tokyo (JP)

(72) Inventors: Yoshitaka Umemoto, Hachioji (JP); Kazuhiko Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 121 days.

(21) Appl. No.: 14/033,820

(22) Filed: Sep. 23, 2013

(65) Prior Publication Data

US 2014/0024890 A1    Jan. 23, 2014

Related U.S. Application Data

(60) Division of application No. 12/541,538, filed on Aug. 14, 2009, now Pat. No. 8,568,295, which is a continuation of application No. PCT/JP2007/071048, filed on Oct. 29, 2007.

(30) Foreign Application Priority Data

Feb. 14, 2007   (JP) .................................. 2007-033825

(51) Int. Cl.
*A61B 1/00* (2006.01)
*A61B 1/018* (2006.01)
(Continued)

(52) U.S. Cl.
CPC .............. *A61B 1/018* (2013.01); *A61B 1/00036* (2013.01); *A61B 1/0057* (2013.01);
(Continued)

(58) Field of Classification Search
CPC ........... A61B 1/00057; A61B 1/00059; A61B 1/00062; A61B 1/0057; A61B 1/018; A61B 1/00147; A61B 1/0036; A61B 1/00149

USPC ................ 600/102, 106, 117, 118, 126, 104; 348/45, 65; 362/574
See application file for complete search history.

(56) References Cited

U.S. PATENT DOCUMENTS 4,422,457 A * 12/1983 Hattori ............................... 606/2
6,932,761 B2 * 8/2005 Maeda et al. .................. 600/152
(Continued)

FOREIGN PATENT DOCUMENTS

| JP | 2000139947 A | 5/2000 |
| JP | 2000152913 A | 6/2000 |

(Continued)

OTHER PUBLICATIONS

Mori (JP 2004/033396) Machine Translation from espacenet.com, 16 pages.*

(Continued)

*Primary Examiner* — Anhtuan T Nguyen
*Assistant Examiner* — Timothy J Neal
(74) *Attorney, Agent, or Firm* — Scully, Scott, Murphy & Presser, P.C.

(57) ABSTRACT

An endoscope system includes at least an endoscope of the endoscope and an accessory, a placement unit on which the endoscope is adapted to be placed, a detecting unit configured to detect whether the endoscope is placed on the placement unit or not, an actuating unit for at least one of the endoscope and the accessory, an operating unit for operating the actuating unit, and a control unit configured to be switched between a normal mode wherein the actuating unit is controlled according to an operation to the operating unit and a restricting mode wherein the actuating unit is controlled regardless of an operation to the operating unit, on the basis of a result of detection by the detecting unit.

8 Claims, 9 Drawing Sheets

(51) Int. Cl.
*A61B 18/14* (2006.01)
*A61B 1/005* (2006.01)
*A61B 1/04* (2006.01)
*A61B 18/12* (2006.01)
*A61B 17/00* (2006.01)

(52) U.S. Cl.
CPC ......... *A61B1/00147* (2013.01); *A61B 18/1492* (2013.01); *A61B 1/00149* (2013.01); *A61B 18/1233* (2013.01); *A61B 2017/00973* (2013.01)

(56) References Cited

U.S. PATENT DOCUMENTS

2005/0192475 A1* 9/2005 Okada .......................... 600/106
2005/0234293 A1 10/2005 Yamamoto et al.

FOREIGN PATENT DOCUMENTS

| | | |
|---|---|---|
| JP | 200433396 A | 2/2004 |
| JP | 2004275321 A | 10/2004 |
| JP | 2005204999 A | 8/2005 |
| JP | 2006506128 A | 2/2006 |
| WO | 2004043256 A2 | 5/2004 |

OTHER PUBLICATIONS

U.S. Office Action dated Nov. 26, 2012 received in related U.S. Appl. No. 12/541,538.
U.S. Office Action dated Mar. 12, 2013 received in related U.S. Appl. No. 12/541,538.
International Search Report dated Jan. 22, 2008 received in corresponding International Application No. PCT/ JP2007/071048.

* cited by examiner

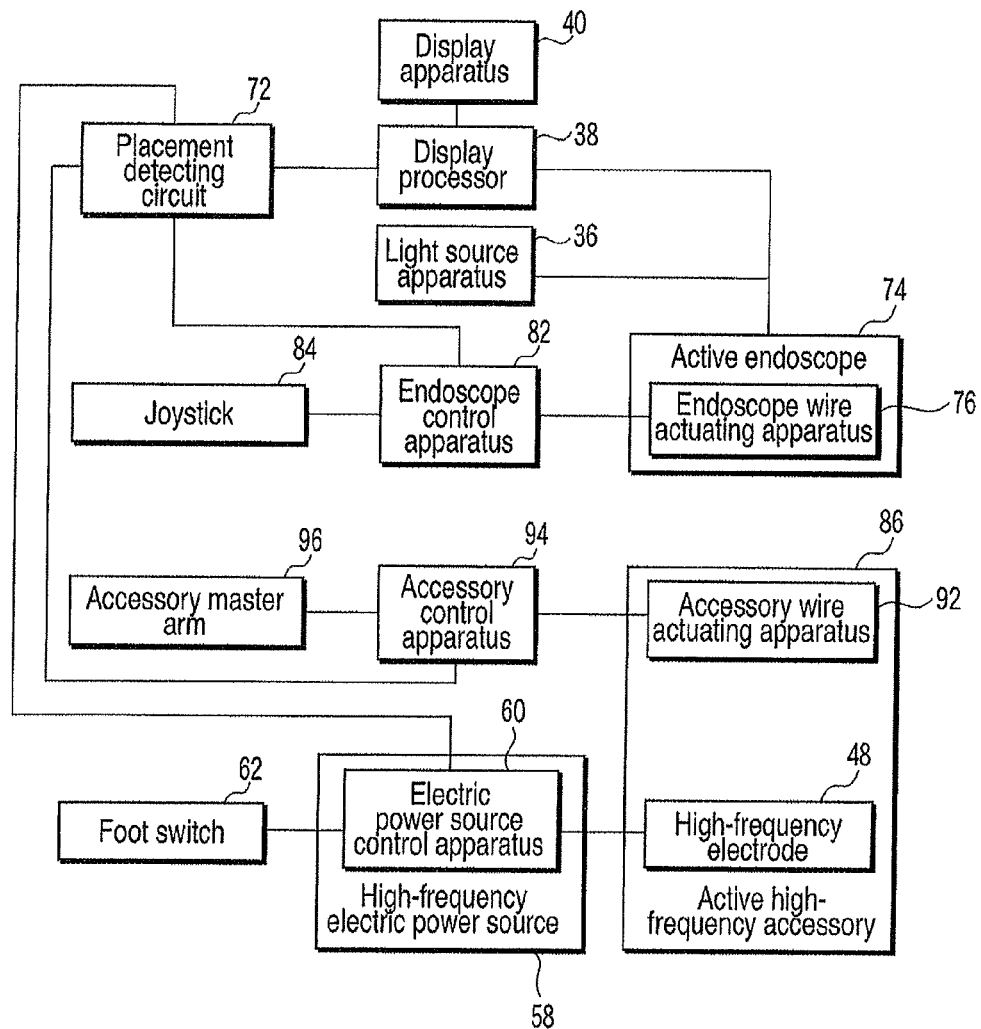
F I G. 7

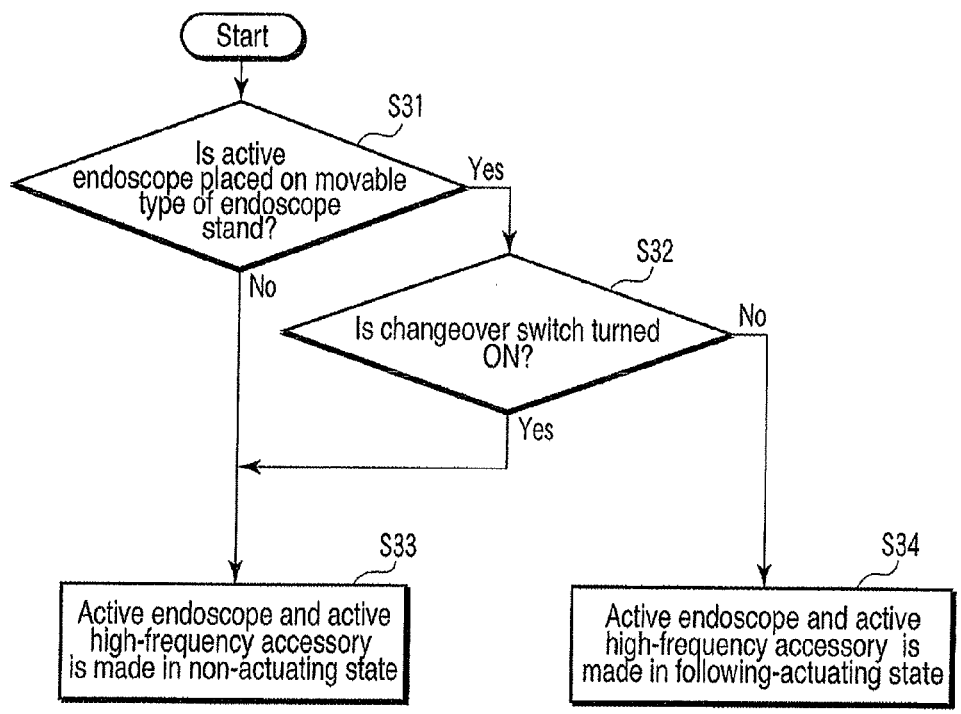
F I G. 10

ENDOSCOPE SYSTEM

CROSS-REFERENCE TO RELATED APPLICATIONS

This application is a Divisional Application of U.S. patent application Ser. No. 12/541,538, filed Aug. 14, 2009, which is a Continuation Application of PCT Application No. PCT/JP2007/071048, filed Oct. 29, 2007, which was published under PCT Article 21(2) in Japanese.

This application is based upon and claims the benefit of priority from prior Japanese Patent Application No. 2007-033825, filed Feb. 14, 2007, the entire contents of each of which are incorporated herein by reference.

BACKGROUND OF THE INVENTION

1. Field of the Invention

The present invention relates to an endoscope system including at least an endoscope of the endoscope and an accessory and further including a placement unit on which the endoscope is placed.

2. Description of the Related Art

Various endoscope systems are used wherein an endoscope and an accessory are inserted into a cavity in the body and perform observation and treatment in the cavity in the body. In such endoscope system, a fixing type of endoscope stand configured to fix the endoscope in a certain position and a movable type of endoscope stand configured to move and fix the endoscope to and in any position may be used.

In Jpn. Pat. Appln. KOKAI Publication No. 2005-204999, a movable type of endoscope stand is disclosed. In the movable type of endoscope stand, arms are coupled in order through joints so as to be rotatable relative to each other. An endoscope can be moved to any position when fixing of the joints is released to enable the arms to be rotated relative to each other and be fixed in any position when the joints are fixed to disable the arms to be rotated relative to each other. In the movable type of endoscope stand disclosed in Jpn. Pat. Appln. KOKAI Publication No. 2005-204999, the fixing of the joints is released only when two switches are simultaneously operated, and therefore, release of the fixing of the joints which an operator does not intend is prevented.

BRIEF SUMMARY OF THE INVENTION

In an aspect of the present invention, an endoscope system includes: at least an endoscope of the endoscope and an accessory; a placement unit on which the endoscope is adapted to be placed; a detecting unit configured to detect whether the endoscope is placed on the placement unit or not; an actuating unit for at least one of the endoscope and the accessory; an operating unit for operating the actuating unit; and a control unit configured to be switched between a normal mode wherein the actuating unit is controlled according to an operation to the operating unit and a restricting mode wherein the actuating unit is controlled regardless of an operation to the operating unit, on the basis of a result of detection by the detecting unit.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a block diagram showing the endoscope system according to the second embodiment of the present invention;

FIG. 10 is a flow chart of a switching actuation control of an active endoscope of the endoscope system according to the third embodiment of the present invention.

DETAILED DESCRIPTION OF THE INVENTION

Figure 1:
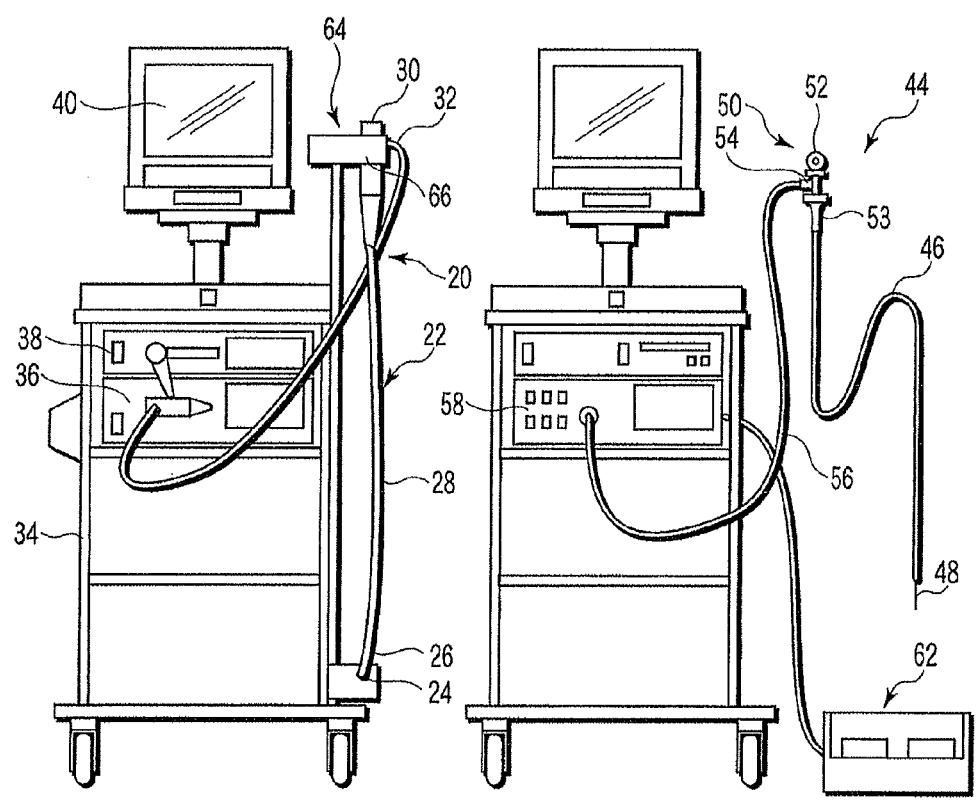
FIG. 1 is a front view showing an endoscope system according to a first embodiment of the present invention.

Hereinafter, each embodiment of the present invention will be explained referring to the drawings.

FIGS. 1 to 4 show a first embodiment of the present invention.

Figure 3:
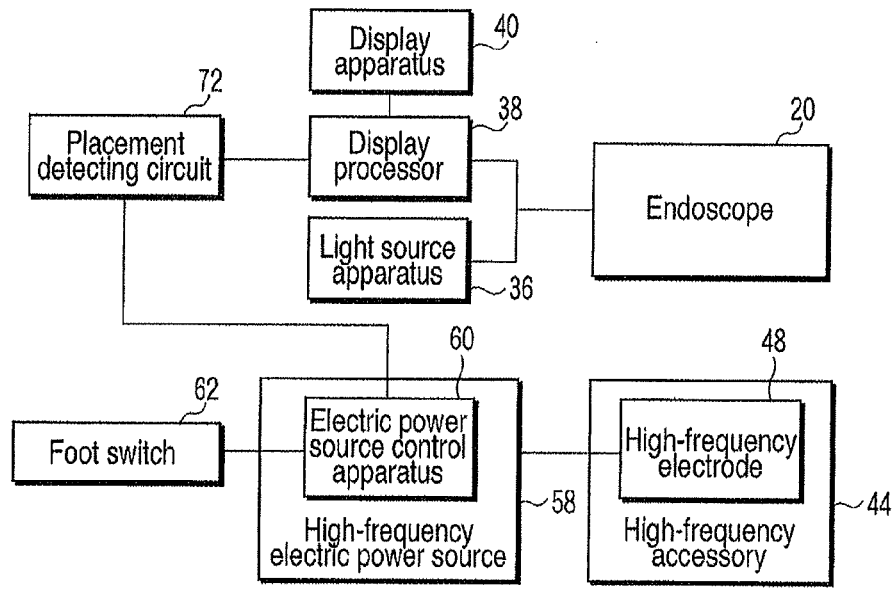
FIG. 3 is a block diagram showing the endoscope system according to the first embodiment of the present invention.

Referring to FIGS. 1 and 3, an endoscope 20 of an endoscope system according to the embodiment includes an endoscope insertion portion 22 configured to be inserted into a cavity in the body. In the endoscope insertion portion 22, a distal end rigid portion 24 being rigid, an endoscope bending portion 26 to be actuated to be bent, an endoscope insertion tube portion 28 being long and flexible are provided in order from the distal end side, and an endoscope operation portion 30 is coupled to the proximal end portion of the endoscope insertion portion 22. A universal cord 32 is extended from the endoscope operation portion 30, and the extended end of the universal cord 32 is connected to a light source apparatus 36 and a display processor 38 carried on an endoscope trolley 34. Illumination light is supplied from the light source apparatus 36 to the endoscope 20 and emitted from the distal end portion of the endoscope 20, an observation image is obtained by an image pick-up unit in the distal end portion of the endoscope 20, an image signal thereof is output to the display processor 38, and the observation image is displayed on a display apparatus 40.

The endoscope operation portion 30 is provided with an accessory insertion opening, and an accessory channel is extended from the accessory insertion opening to the distal end portion of the endoscope 20.

A high-frequency accessory 44 as an energy accessory is configured to be inserted through an accessory channel of the endoscope 20. In the high-frequency accessory 44, a high-frequency electrode 48 is provided on the distal end portion of an accessory insertion tube portion 46 being long and flexible and configured to be projected and retracted relative to it. The distal end portion of an accessory operation wire is coupled to the high-frequency electrode 48. The accessory operation wire is configured to operate the high-frequency electrode 48 to be moved forward and backward and apply a high-frequency current to the high-frequency electrode 48, and is inserted through the accessory insertion tube portion 46 and extended to the distal end side. The proximal end portion of the accessory operation wire is connected to a slider 52 in an accessory operation portion 50 coupled to the proximal end portion of the accessory insertion tube portion 46. When the slider 52 is moved forward and backward relative to the accessory operation portion main portion 53, the accessory operation wire is moved forward and backward. Moreover, a connecting contact 54 is provided on the slider 52 and electrically connected to the accessory operation wire. The connecting contact 54 is connected to a high-frequency electric power source 58 as an energy output apparatus through an electric power source code 56. An electric power source control apparatus 60 as an energy output control apparatus is built in the high-frequency electric power source 58, and a foot switch 62 as an energy output instructing input apparatus is connected to the electric power source control apparatus 60.

Moreover, a fixing type of endoscope stand 64 as a placement unit is provided on the endoscope trolley 34 and is configured to fix the endoscope operation portion 30 of the endoscope 20 placed thereon in a certain position.

Figure 2A:
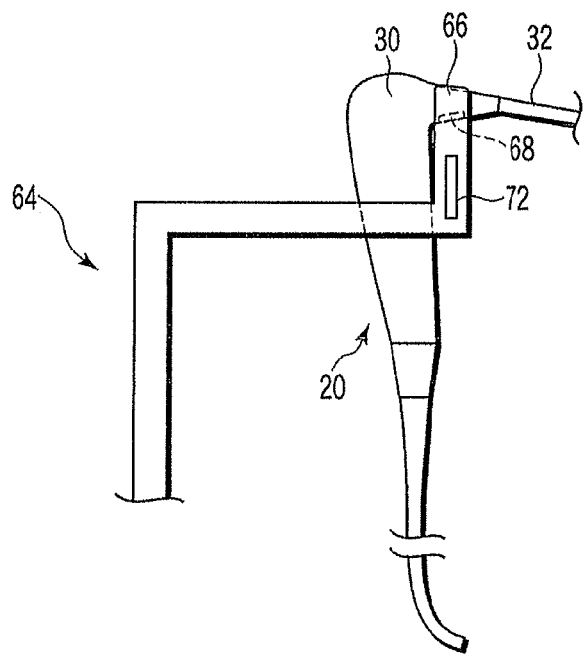
FIG. 2A is a schematic front view showing a detecting unit of the endoscope system according to the first embodiment of the present invention.
Figure 2B:
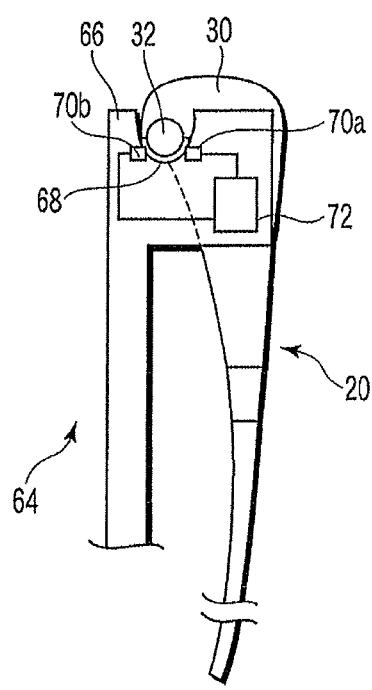
FIG. 2B is a schematic side view showing the detecting unit of the endoscope system according to the first embodiment of the present invention.

Referring to FIGS. 2A and 2B, and 3, a concave shaped placement portion 66 is provided in the fixing type of endoscope stand 64 and the proximal end portion of the universal cord 32 of the endoscope operation portion 30 is configured to be hanged thereon.

A detecting unit is provided on the fixing type of endoscope stand 64 and configured to detect whether the endoscope 20 is placed on the fixing type of endoscope stand 64 or not. That is, a metal plate 68 is provided on the proximal end portion of the universal cord 32 of the endoscope 20, and a pair of electrodes 70A and 70B is provided on the placement portion 66 of the fixing type of endoscope stand 64 and configured to be electrically connected to each other through the metal plate 68 when the proximal end portion of the universal cord 32 is hanged on the placement portion 66. A placement detecting circuit 72 is connected to the pair of electrodes 70A and 70B. The placement detecting circuit 72 is configured to detect whether the endoscope 20 is placed on the fixing type of endoscope stand 64 or not on the basis of whether the pair of electrodes 70A and 70B is electrically connected to each other or not. It is noted that various detecting unit may be used as a detecting unit other than the detecting unit using the resistance sensor, for example, a gravity sensor or a pressure sensor is provided on the placement portion 66 and a measurement parameter may be detected which is varied due to the weight of the endoscope 20 when the endoscope 20 is placed on the placement portion 66.

The placement detecting circuit 72 is configured to output a placement state signal indicating a placement state to the electric power source control apparatus 60 of the high-frequency electric power source 58. The electric power source control apparatus 60 is configured to be changed to a normal mode when it receives a placement state signal indicating non-placement, and actuate and stop the high-frequency electric power source 58 according to turning ON and OFF the foot switch 62. On the other hand, the electric power source control apparatus 60 is configured to be changed to a restricting mode when it receives a placement state signal indicating placement, and not to actuate the high-frequency electric power source 58 regardless of turning ON the foot switch 62. It is noted that the electric power source control apparatus 60 configured to judge that the endoscope 20 is not placed on the fixing type of endoscope stand 64 and be changed to the normal mode when it does not receive a placement state signal.

It is noted that the placement detecting circuit 72 is also configured to output a placement state signal to the display processor 38. The display processor 38 is configured to display an image such as letters and colors indicating that the endoscope 20 is placed on the fixing type of endoscope stand 64 on the display apparatus 40 when it receives a placement state signal indicating placement.

Next, a method for controlling the endoscope system according to the embodiment will be explained.

Figure 4:
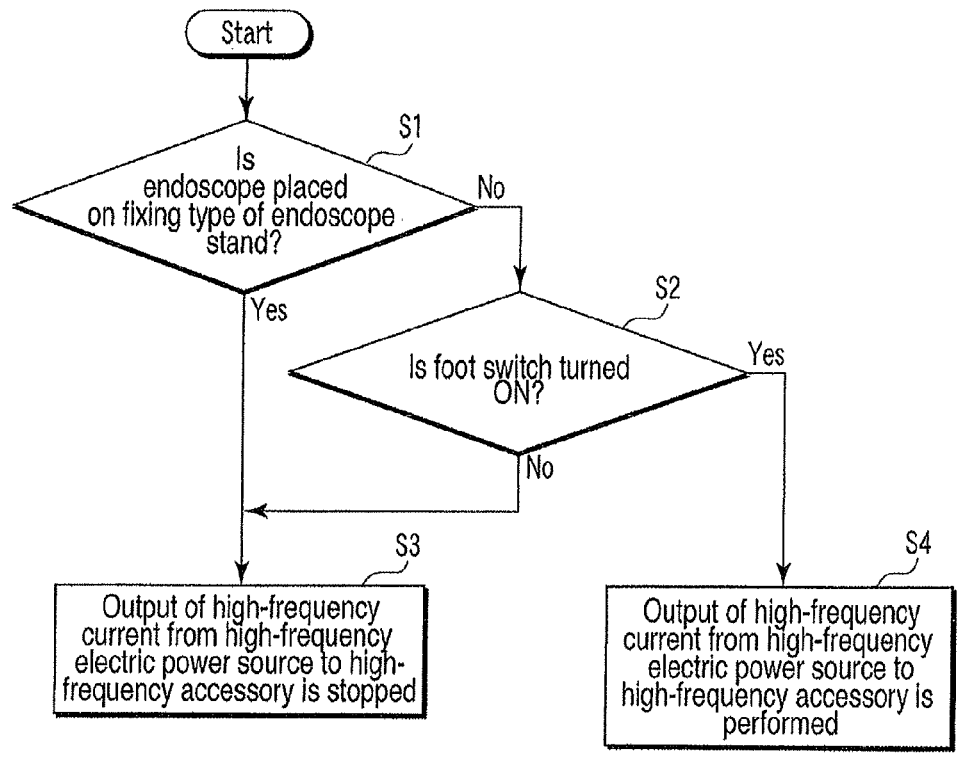
FIG. 4 is a flow chart of an output actuation control of a high-frequency accessory of the endoscope system according to the first embodiment of the present invention.

Referring to a flow chart in FIG. 4, output actuation control of the high-frequency accessory 44 will be explained.

Step 1 (S1)

The placement detecting circuit 72 detects whether the endoscope 20 is placed on the fixing type of endoscope stand 64 or not. The step returns to Step 2 (S2) when the endoscope 20 is not placed on the fixing type of endoscope stand 64 and the step advances to Step 3 (S3) when it is placed.

Step 2 (S2)

The electric power source control apparatus 60 detects whether the foot switch 62 is turned ON or not. The step returns to Step 3 (S3) when the foot switch 62 is not turned ON and the step advances to Step 4 (S4) when it is turned ON.

Step 3 (S3)

The electric power source control apparatus 60 stops an actuation of the high-frequency electric power source 58 to stop output of a high-frequency current from the high-frequency electric power source 58 to the high-frequency accessory 44 when the endoscope 20 is placed on the fixing type of endoscope stand 64 or when it is not placed and the foot switch 62 is not turned ON.

Step 4 (S4)

The electric power source control apparatus 60 actuates the high-frequency electric power source 58 to output a high-frequency current from the high-frequency electric power source 58 to the high-frequency accessory 44 when the endoscope 20 is not placed on the fixing type of endoscope stand 64 and the foot switch 62 is turned ON.

Therefore, the endoscope system according to the embodiment exhibits the following effect.

In the endoscope system according to the embodiment, the endoscope 20 is placed on the fixing type of endoscope stand 64 when the endoscope 20 is not used, and output of a high-frequency current from the high-frequency electric power source 58 to the high-frequency accessory 44 is stopped regardless of turning ON the foot switch 62 when the endoscope 20 is placed on the fixing type of endoscope stand 64. Therefore, it is prevented that a high-frequency current is output to the high-frequency accessory 44 when the endoscope 20 is not used.

FIGS. 5 to 8B show a second embodiment of the present invention.

Figure 5:
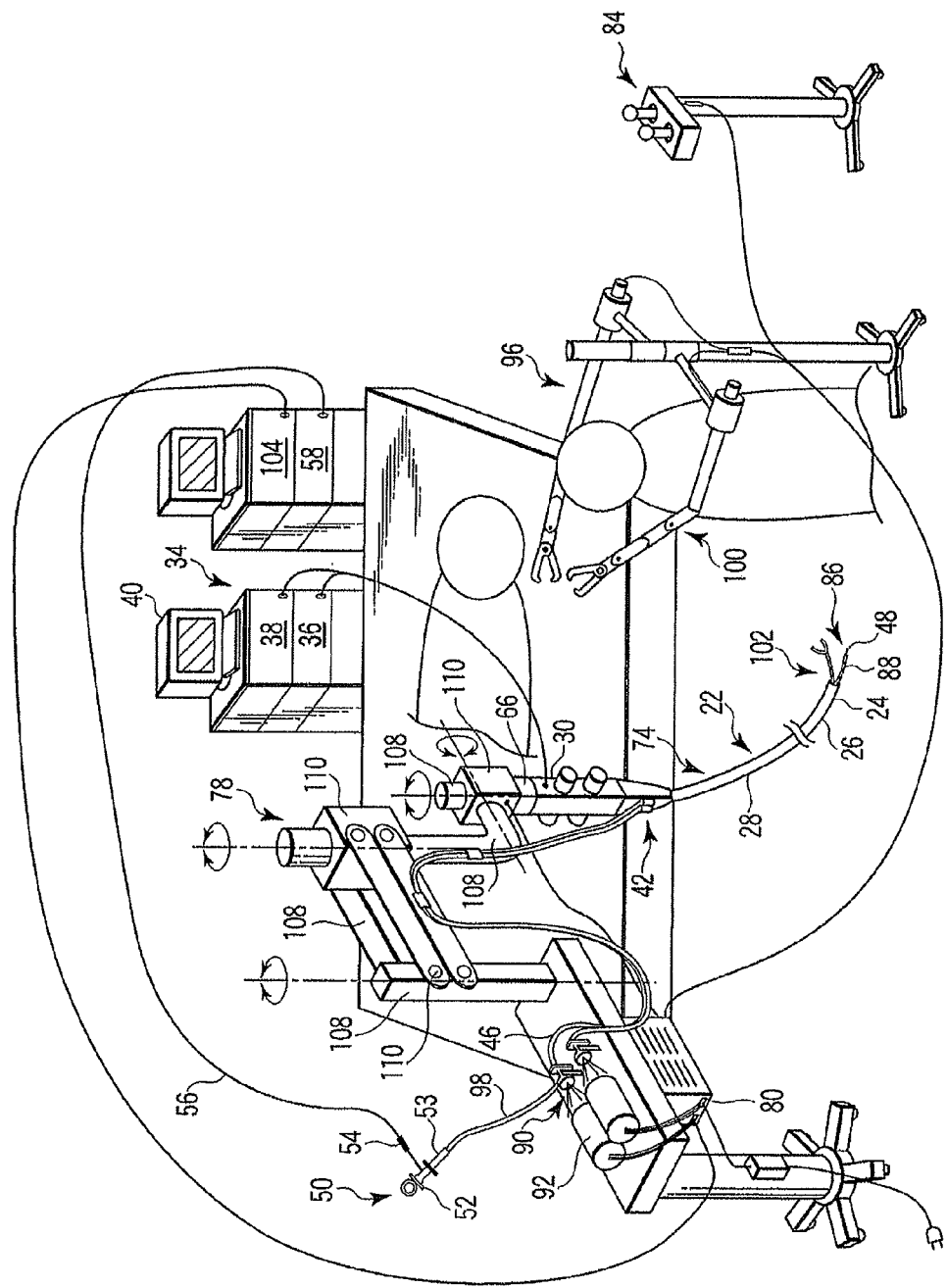
FIG. 5 is a perspective view showing an endoscope system according to a second embodiment of the present invention.

Referring to FIGS. 5 and 7, an endoscope system according to the embodiment includes an active endoscope 74. The active endoscope 74 is an endoscope wherein an endoscope active mechanism is added to the endoscope 20 according to the first embodiment. That is, a group of endoscope angle wires is inserted through an endoscope bending portion 26 and an endoscope insertion tube portion 28 of the active endoscope 74 and configured to operate the endoscope bending portion 26 to be bend. The group of the endoscope angle wires is put from the endoscope insertion tube portion 28 into an endoscope operation portion 30 and coupled to an endoscope wire actuating apparatus 76 in the endoscope operation portion 30. The endoscope wire actuating apparatus 76 is connected to an endoscope control apparatus 82 of a control unit 80 provided on a movable type of endoscope stand 78, and a joystick 84 as an endoscope following instructing input apparatus is connected to the endoscope control apparatus 82. When the joystick 84 is operated, the endoscope wire actuating apparatus 76 moves forward and backward the group of endoscope angle wires and the endoscope bending portion 26 is actuated to be bend according to an operation to the joystick 84. As is mentioned above, the endoscope wire actuating apparatus 76, the group of endoscope angle wires and the endoscope bending portion 26 form an endoscope active mechanism.

The active endoscope 74 is connected to a light source apparatus 36 and a display processor 38 carried on an endoscope trolley 34 as is similar to the endoscope 20 according to the first embodiment.

Furthermore, the endoscope system according to the embodiment includes an active high-frequency accessory 86 as an energy accessory and an active accessory configured to be inserted through an accessory channel of the active endoscope 74. The active high-frequency accessory 86 is an accessory wherein an accessory active mechanism is added to the high-frequency accessory 44 according to the first embodiment. That is, in the active high-frequency accessory 86, an accessory bending portion 88 is coupled to the distal end portion of an accessory insertion tube portion 46, and a high-frequency electrode 48 is provided on the distal end portion of the accessory bending portion 88. A group of accessory angle wires 90 is inserted through the accessory bending portion 88 and the accessory insertion tube portion 46 and configured to actuate the accessory bending portion 88 to be bend. The accessory insertion tube portion 46 is put out from an accessory insertion opening 42 of the active endoscope 74 and extended to an accessory wire actuating apparatus 92 provided on the movable type of endoscope stand 78, and the group of accessory angle wires 90 is put out from the proximal end portion of the accessory insertion tube portion 46 and coupled to the accessory wire actuating apparatus 92. The accessory wire actuating apparatus 92 is connected to an accessory control apparatus 94 of the control unit 80, and an accessory master arm 96 as an accessory following instructing input apparatus is connected to the accessory control apparatus 94. The accessory master arm 96 has a similar degree of freedom to that of the accessory bending portion 88 of the active high-frequency accessory 86. When the accessory master arm 96 is operated, the accessory wire actuating apparatus 92 moves forward and backward the group of accessory angle wires 90 and the accessory bending portion 88 is actuated to be bend following an operation to the accessory master arm 96. As is mentioned above, the accessory wire actuating apparatus 92, the group of accessory angle wires 90 and the accessory bending portion 88 form an accessory active mechanism.

A flexible tube 98 is extended from the proximal end portion of the accessory insertion tube portion 46, and an accessory operation wire is inserted through the flexible tube 98. As is similar to the first embodiment, an accessory operation portion 50 is coupled to the proximal end portion of the flexible tube 98, and the accessory operation portion 50 is connected to a high-frequency electric power source 58 through an electric power source code 56.

It is noted that an active grasping forceps 102 is inserted through a forceps channel of the active endoscope 74 and is configured to be operated by a forceps master arm 100. A personal computer 104 is connected to the control unit 80 and is configured to perform various kinds of arithmetic and storage processing.

Furthermore, the endoscope system according to the embodiment includes the movable type of endoscope stand 78. The endoscope operation portion 30 of the active endoscope 74 is adapted to be placed on the distal end portion of the movable type of endoscope stand 78 so as to be attachable and detachable thereto. The movable type of endoscope stand 78 is configured to move and fix the endoscope operation portion 30 placed thereon to and in any position. That is, in the movable type of endoscope stand 78, arms 108 are coupled in order through joints 110 so as to be rotatable relative to each other. The endoscope operation portion 30 can be moved to any position when fixing of the joints 110 is released to enable the arms 108 to be rotated relative to each other and be fixed in any position when the joints 110 are fixed to disable the arms 108 to be rotated relative to each other.

Figure 6:
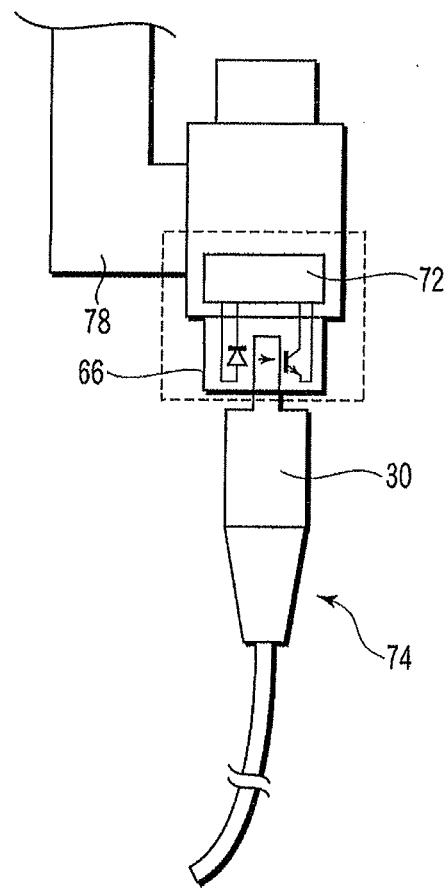
FIG. 6 is a schematic side view showing a detecting unit of the endoscope system according to the second embodiment of the present invention.

Referring to FIGS. 6 and 7, a placement portion 66 is provided on the distal end portion of the movable type of endoscope stand 78 and the endoscope operation portion 30 is adapted to be placed thereon so as to be attachable and detachable. A placement detecting circuit 72 as a detecting unit is provided on the placement portion 66 and configured to detect whether the active endoscope 74 is placed on the movable type of endoscope stand 78 or not.

The placement detecting circuit 72 is configured to output a placement state signal indicating a placement state to an electric power source control apparatus 60 of the high-frequency electric power source 58. The electric power source control apparatus 60 is configured to be changed to a normal mode and actuate the high-frequency electric power source 58 according to turning ON the foot switch 62 when it receives placement state signal indicating placement. On the other hand, the electric power source control apparatus 60 is configured to be changed to a restricting mode and not to actuate the high-frequency electric power source 58 regardless of turning ON the foot switch 62 when it receives a placement state signal indicating non-placement.

Moreover, the placement detecting circuit 72 is configured to output a placement state signal to the endoscope control apparatus 82. The endoscope control apparatus 82 is configured to be changed to a normal mode and make the endoscope active mechanism perform a following actuation according to an operation to the joystick 84 when it receives a placement state signal indicating placement. On the other hand, the endoscope control apparatus 82 is configured to be changed to a restricting mode and stop a following actuation of the endoscope active mechanism regardless of an operation to the joystick 84 when it receives a placement state signal indicating non-placement.

The placement detecting circuit 72 is also configured to output a placement state signal to the accessory control apparatus 94. The accessory control apparatus 94 is configured to be changed to a normal mode when it receives a placement state signal indicating placement and to a restricting mode when it receives a placement state signal indicating non-placement.

It is noted that the endoscope control apparatus 82, the electric power source control apparatus 60 and the accessory control apparatus 94 is configured to judge that the endoscope 20 is not placed on the movable type of endoscope stand 78 and be changed to the restricting mode, when it does not receive a placement state signal.

Next, a method for controlling the endoscope system according to the embodiment will be explained.

Figure 8A:
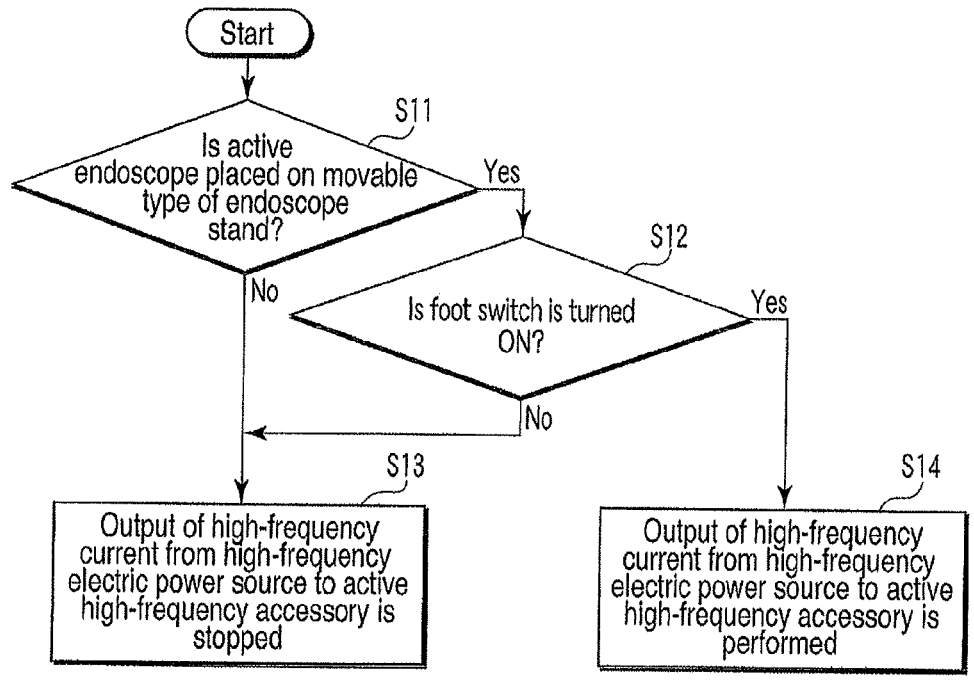
FIG. 8A is a flow chart of an output actuation control of an active high-frequency accessory of the endoscope system according to the second embodiment of the present invention.

Referring to FIG. 8A, output actuation control of the active high-frequency accessory 86 will be explained.

Step 11 (S11)

The placement detecting circuit 72 detects whether the active endoscope 74 is placed on the movable type of endoscope stand 78 or not. The step advances to Step 12 (S12) when the active endoscope 74 is placed on the movable type of endoscope stand 78 and the step advances to Step 13 (S13) when it is not placed.

Step 12 (S12)

The electric power source control apparatus 60 detects whether the foot switch 62 is turned ON or not. The step advances to Step 13 (S13) when the foot switch 62 is not turned ON and the step advances to Step 14 (S14) when it is turned ON.

Step 13 (S13)

The electric power source control apparatus 60 stops an actuation of the high-frequency electric power source 58 to stop output of a high-frequency current from the high-frequency electric power source 58 to the high-frequency accessory 44 when the active endoscope 74 is not placed on the movable type of endoscope stand 78 or when it is placed and the foot switch 62 is not turned ON.

Step 14 (S14)

The electric power source control apparatus 60 actuates the high-frequency electric power source 58 to output a high-frequency current from the high-frequency electric power source 58 to the high-frequency accessory 44 when the active endoscope 74 is placed on the movable type of endoscope stand 78 and the foot switch 62 is turned ON.

Figure 8B:
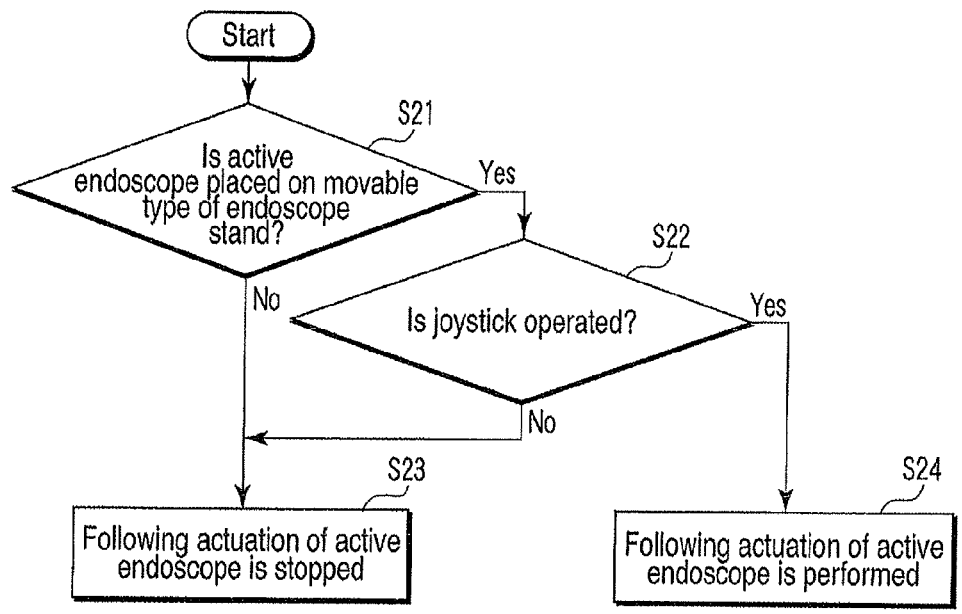
FIG. 8B is a flow chart of a following actuation control of an active endoscope of the endoscope system according to the second embodiment of the present invention.

Referring to FIG. 8B, following actuation control of the active endoscope 74 will be explained.

Step 21 (S21)

The placement detecting circuit 72 detects whether the active endoscope 74 is placed on the movable type of endoscope stand 78 or not. The step advances to Step 22 (S22) when the active endoscope 74 is placed on the movable type of endoscope stand 78 and the step advances to Step 23 (S23) when it is not placed.

Step 22 (S22)

The endoscope control apparatus 82 detects whether the joystick 84 is operated or not. The step advances to Step 23 (S23) when the joystick 84 is operated and the step advances to Step 24 (S24) when it is operated.

Step 23 (S23)

The endoscope control apparatus 82 stops a following actuation of the endoscope active mechanism to stop a following actuation of the active endoscope 74 when the endoscope 20 is placed on the movable type of endoscope stand 78 or when it is placed and the joystick 84 is not operated.

Step 24 (S24)

The endoscope control apparatus 82 makes the endoscope active mechanism perform a following actuation to make the active endoscope 74 perform a following actuation when the active endoscope 74 is placed on the movable type of endoscope stand 78 and the joystick 84 is operated.

Following actuation control of the active high-frequency accessory 86 is similar to the following actuation control of the active endoscope 74.

Therefore, the endoscope system according to the embodiment exhibits the following effect.

In the endoscope system according to the embodiment, the active endoscope 74 is placed on the movable type of endoscope stand 78 when the active endoscope 74 is normally used. Output of a high-frequency current from the high-frequency electric power source 58 to the high-frequency accessory 44 and following actuations of the active endoscope 74 and the active high-frequency accessory 86 are stopped regardless of operations to the foot switch 62, the joystick 84 and the accessory master arm 96 when the active endoscope 74 is not placed on the movable type of endoscope stand 78. Therefore, it is prevented that a high-frequency current is output to the high-frequency accessory 44, and the active endoscope 74 and the active high-frequency accessory 86 are made to perform following actuations, in the time other than the time when the active endoscope 74 is normally used.

Figure 9:
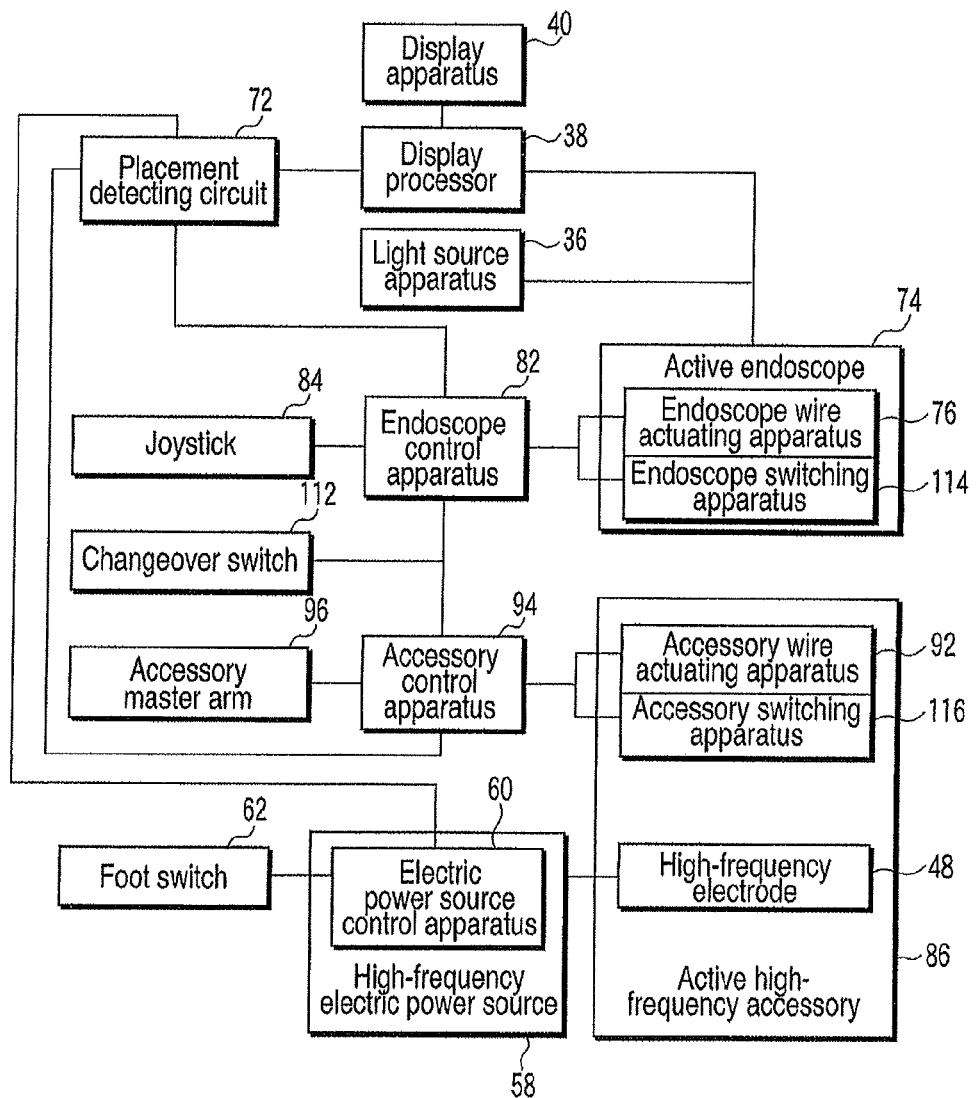
FIG. 9 is a block diagram showing an endoscope system according to a third embodiment of the present invention.

FIGS. 9 and 10 show a third embodiment of the present invention.

An endoscope system according to the embodiment is an endoscope system wherein the following composition is added to the endoscope system according to the second embodiment.

A changeover switch 112 as an endoscope switching instructing input apparatus and an accessory switching instructing input apparatus is connected to an endoscope control apparatus 82 and an accessory control apparatus 94. On the other hand, in an endoscope active mechanism and an accessory active mechanism, an endoscope switching apparatus 114 and an accessory switching apparatus 116 are provided on an endoscope wire actuating apparatus 76 and an accessory wire actuating apparatus 92, respectively.

When the changeover switch 112 is operated, the endoscope control apparatus 82 makes the endoscope switching apparatus 114 perform a switching actuation to switch the endoscope active mechanism between a following-actuating state and a non-actuating state. In the following-actuating state, the endoscope control apparatus 82 makes the endoscope active mechanism perform a following actuation according to an operation to a joystick 84. In the non-actuating state, the endoscope active mechanism is not made to perform a following actuation regardless of an operation to the joystick 84. Moreover, a fixing state or a releasing state is selected as a non-actuating state of the endoscope active mechanism. In the fixing state, the endoscope wire actuating apparatus 76 fixes a group of endoscope angle wires to fix an endoscope bending portion 26 so as to be unable to be bent. On the other hand, in the releasing state, the endoscope wire actuating apparatus 76 releases the group of endoscope angle wires to be able to be moved forward and backward to release the endoscope bending portion 26 so as to be able to be bend.

As is similar to this, when the changeover switch 112 is operated, the accessory control apparatus 94 also makes the accessory switching apparatus 116 perform a switching actuation to switch the accessory active mechanism between a following-actuating state and a non-actuating state. Moreover, a fixing state or a releasing state is selected as a non-actuating state of the accessory active mechanism.

Furthermore, the endoscope control apparatus 82 is configured to be changed to a normal mode and make the endoscope switching apparatus 114 perform a switching actuation to switch the endoscope active mechanism between the following-actuating state and the non-actuating state according to an operation to the changeover switch 112 when it receives a placement state signal indicating placement. On the other hand, the endoscope control apparatus 82 is configured to be changed to a restricting mode and make the endoscope switching apparatus 114 perform a switching actuation to switch the endoscope active mechanism to the non-actuating state (the fixing state or the releasing state) regardless of an operation to the changeover switch 112 when it receives a placement state signal indicating non-placement.

As is similar to this, the accessory control apparatus 94 is configured to be changed to a normal mode when it receives a placement state signal indicating placement and to a restricting mode when it receives a placement state signal indicating non-placement.

Next, a method for controlling the endoscope system according to the embodiment will be explained.

Referring to FIG. 10, switching actuation control of the active endoscope 74 and the active high-frequency accessory 86 will be explained.

Step 31 (S31)

The placement detecting circuit 72 detects whether the active endoscope 74 is placed on the movable type of endoscope stand 78 or not. The step advances to Step 32 (S32) when the active endoscope 74 is placed on the movable type of endoscope stand 78 and the step advances to Step 33 (S33) when it is not placed.

Step 32 (S32)

The endoscope control apparatus 82 and the accessory control apparatus 94 detects whether the changeover switch 112 is turned ON or not. The step advances to Step 33 (S33) when the changeover switch 112 is turned ON and the step advances to Step 34 (S34) when it is not turned ON.

Step 33 (S33)

The endoscope control apparatus 82 and the accessory control apparatus 94 make the endoscope switching apparatus 114 and the accessory switching apparatus 116 perform switching actuations to make the endoscope active mechanism and the accessory active mechanism in the non-actuating state (the fixing state or the releasing state), and therefore, the active endoscope 74 and the active high-frequency accessory 86 is made in the non-actuating state (the fixing state or the releasing state), when the active endoscope 74 is not placed on the movable type of endoscope stand 78 or when it is placed and the changeover switch 112 is turned ON.

Step 34 (S34)

The endoscope control apparatus 82 and the accessory control apparatus 94 make the endoscope switching apparatus 114 and the accessory switching apparatus 116 perform switching actuations to make the endoscope active mechanism and the accessory active mechanism in the following-actuating state, and therefore, the active endoscope 74 and the active high-frequency accessory 86 is made in the following-actuating state, when the active endoscope 74 is placed on the movable type of endoscope stand 78 and the changeover switch 112 is turned ON. Then, the endoscope control apparatus 82 and the accessory control apparatus 94 make the active endoscope 74 and the active high-frequency accessory 86 perform the following actuation according to operations to the joystick 84 and the accessory master arm 96.

Therefore, the endoscope system according to the embodiment exhibits the following effects.

In the endoscope system according to the embodiment, the endoscope 20 is placed on the movable type of endoscope stand 78 when the endoscope 20 is normally used. The active endoscope 74 and the active high-frequency accessory 86 is made in the non-actuating state (the fixing state or the releasing state) regardless of an operation to the changeover switch 112 when the active endoscope 74 is not placed on the movable type of endoscope stand 78. Therefore, it is prevented that the active endoscope 74 and the active high-frequency accessory 86 are switched to the following-actuating state and then perform following actuations in the time other than the time when the endoscope 20 is normally used.

In particular, in the case where the fixing state is selected as the non-actuating states of the active endoscope 74 and the active high-frequency accessory 86, the active endoscope 74 and the active high-frequency accessory 86 is automatically switched to the fixing state when the active endoscope 74 is detached from the movable type of endoscope stand 78. That is, it is possible to keep attitudes of the active endoscope 74 and the active high-frequency accessory 86 without turning ON the changeover switch 112 when the active endoscope 74 is detached from the movable type of endoscope stand 78.

Moreover, in the case where the releasing state is selected as the non-actuating states of the active endoscope 74 and the active high-frequency accessory 86, the active endoscope 74 and the active high-frequency accessory 86 is automatically switched to the releasing state when the active endoscope 74 is detached from the movable type of endoscope stand 78. That is, it is possible to pull out the active high-frequency accessory 86 or the active endoscope 74 from the accessory channel or a cavity in the body without turning ON the changeover switch 112 when the active endoscope 74 is detached from the movable type of endoscope stand 78. Therefore, it is possible to rapidly pull out the active high-frequency accessory 86 and the active endoscope 74.

The present invention is applicable to various energy accessories other than the high-frequency accessory 44, for example, an ultrasonic accessory.

Moreover, it is possible to combine the fixing type of endoscope stand 64 and the active endoscope 74 or the active high-frequency accessory 86. That is, a following actuation of the active endoscope 74 or the active high-frequency accessory 86 is stopped, or the active endoscope 74 or the active high-frequency accessory 86 is made in the non-actuating state, when the endoscope 20 or the active endoscope 74 is placed on the fixing type of endoscope stand 64, and therefore, it is prevented that a following actuation of the active endoscope 74 or the active high-frequency accessory 86 is performed when the endoscope 20 or the active endoscope 74 is not used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an endoscope;
   an accessory;
   an accessory actuating unit configured to actuate the accessory by an output from an electric power source;
   a foot switch which is connected to the electric power source and which is configured to mechanically turn ON and OFF to actuate and stop, respectively, the electric power source according to turning the foot switch ON and OFF;
   a placement portion on which the endoscope is adapted to be placed and the placement portion being configured to move and fix the endoscope to and in any position;
   a detecting unit configured to detect whether or not the endoscope is placed on the placement portion;
   an operating unit configured to operate the accessory actuating unit; and
   a control unit configured to be switched between a normal mode wherein the accessory actuating unit is actuated according to an operation to the operating unit when the detecting unit detects that the endoscope is placed on the placement portion and a restricting mode wherein the accessory actuating unit is not actuated regardless of an operation to the operating unit, on the basis of a result of detection by the detecting unit, the control unit being configured to be switched to the restricting mode when the detecting unit detects that the endoscope is not placed on the placement portion regardless of turning ON the foot switch, wherein the control unit prevents the accessory actuating unit from being switched to a following-actuating state and performs a following actuation of the accessory to the endoscope in a time other than a time in the normal mode when the endoscope is normally used in the normal mode.

2. The endoscope system according to claim 1, wherein the accessory actuating unit includes an accessory wire configured to operate the accessory and an accessory wire actuating apparatus configured to actuate the accessory wire, and the control unit is configured to be switched between the normal mode wherein the accessory wire actuating apparatus is actuated according to the operation to the operating unit and the restricting mode wherein the accessory wire actuating apparatus is not actuated regardless of the operation to the operating unit, on the basis of the result of detection by the detecting unit.

3. The endoscope system according to claim 2, wherein the control unit is configured to make the accessory perform the following actuation according to an operation to the operation unit in the normal mode and is configured to fix the accessory wire to be moved forward and backward regardless of an operation to the operation unit in the restricting mode.

4. The endoscope system according to claim 2, wherein the control unit is configured to make the accessory perform the following actuation according to an operation to the operation unit in the normal mode and is configured to release the accessory wire to be moved forward and backward regardless of an operation to the operation unit in the restricting mode.

5. The endoscope system according to claim 1, further comprising an endoscope wire actuating unit configured to actuate an endoscope wire which is configured to operate a bending portion of the endoscope, wherein:

the operation unit is configured to operate the endoscope wire actuating unit, and the control unit is configured to make the bending portion perform the following actuation according to an operation to the operation unit in the normal mode and is configured to fix the endoscope wire to be moved forward and backward regardless of an operation to the operation unit in the restricting mode.

6. The endoscope system according to claim 1, further comprising an endoscope wire configured to operate a bending portion of the endoscope, and an endoscope wire actuating unit configured to actuate the endoscope wire, wherein:

the operation unit is configured to operate the endoscope wire actuating unit, and the control unit is configured to make the bending portion perform the following actuation according to an operation to the operation unit in the normal mode and is configured to release the endoscope wire to be moved forward and backward regardless of an operation to the operation unit in the restricting mode.

7. The endoscope system according to claim 1, further comprising a changeover switch which is connected to the control unit and which is configured to switch the accessory actuating unit between a following-actuating state and a non-actuating state.

8. The endoscope system according to claim 7, wherein the non-actuating state is configured to select one of a fixing state which fixes the accessory actuating unit and a releasing state which releases the accessory actuating unit.

* * * * *